United States Patent [19]

Kerr

[11] 4,047,930
[45] Sept. 13, 1977

[54] METHOD OF STERILIZING MALE ANTHERS

[75] Inventor: Michael W. Kerr, Borden, England
[73] Assignee: Shell Oil Company, Houston, Tex.
[21] Appl. No.: 721,001
[22] Filed: Sept. 7, 1976
[30] Foreign Application Priority Data
   Sept. 16, 1975 United Kingdom .............. 38011/75
[51] Int. Cl.$^2$ ............................................. A01N 9/22
[52] U.S. Cl. ............................................. 71/95; 71/76
[58] Field of Search ...................................... 71/76, 95
[56] References Cited

U.S. PATENT DOCUMENTS

| | | | |
|---|---|---|---|
| 2,889,662 | 6/1959 | Eaton et al. | 71/95 |
| 3,136,620 | 6/1964 | Bucha et al. | 71/95 |
| 3,149,954 | 9/1964 | Harrod | 71/95 |

FOREIGN PATENT DOCUMENTS

| | | | |
|---|---|---|---|
| 298,311 | 5/1972 | U.S.S.R. | 71/95 |

OTHER PUBLICATIONS

Rowland et al. I, "Inhibition of Bacterial, etc.," (1972) CA 77 No. 14817y, (1972).
Rowland et al. II, "Specificity of the *E. coli* etc.," (1975) CA 83 No. 158,457c, (1975).

*Primary Examiner*—Glennon H. Hollrah

[57] ABSTRACT

Compounds of the formula

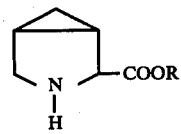

wherein R is hydrogen, alkyl, a metal ion, ammonium or alkylammonium, are useful for sterilizing male anthers in plants.

4 Claims, No Drawings

METHOD OF STERILIZING MALE ANTHERS

BACKGROUND OF THE INVENTION

1. Field of the Invention

This invention relates to a method of sterilizing male anthers in plants, especially in plants of small grain cereal crops, and to a composition therefor.

2. Description of the Prior Art

To obtain high-yielding hybrid seeds, seed-breeders cross-pollinate carefully selected parents, an operation which is very time-consuming and requires highly-skilled staff especially in the case of small-grain cereals which have hermaphroditic flowers and normally self-pollinate. Generally speaking a small-grain cereal hybrid can only be obtained if self-pollination is completely avoided and in practice this is achieved by removing the male anthers from the cereal flowers by hand. Accordingly, if the flowers could be treated in such a way that the male anthers were sterilized without affecting female fertility, then this would represent a considerable advance in the seed-breeding industry.

The Applicant has now found a group of heterocyclic compounds which when applied to plants, and especially to small-grain cereal crops selectively sterilize the male anthers.

SUMMARY OF THE INVENTION

Accordingly, the present invention provides a method of sterilizing male anthers in plants which comprises treating plants with a heterocyclic compound having the following general formula:

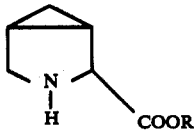

(I)

wherein R represents a hydrogen atom, an alkali metal, an alkaline earth metal, ammonium, alkylammonium the alkyl group or groups of which preferably each contain up to 6 carbon atoms, or an alkyl group of up to 10 carbon atoms, preferably up to 4 carbon atoms. When R represents a metal ion this is preferably a sodium or potassium ion but other metal ions may be employed, if desired.

The preferred compounds for sterilizing male anthers of plants and especially of small-grain cereal plants are 2-carboxy-3,4-methano-pyrrolidine.

The heterocyclic compounds may be applied to the plants at a number of stages in their development, suitably during the period between the 2-node stage of the plant and just before emergence of the ear, i.e., during the stem extension period of the plant. When applied during this period substantially complete sterilization of the male anthers occurs.

The compounds are preferably applied to small-grain cereals such as wheat, barley, oat, rye, rice and millet, but can also be applid to large-grain cereals, such as maize and sorghum.

The compounds may be applied to the plants as such but, as is normal practice in the application of chemicals to plants, it is preferred to apply the compound in the form of a composition which in addition to the compound also comprises a carrier or a surface-active agent or both a carrier and a surface-active agent.

The Applicant has also found that when a heterocyclic compound of the general formula I is applied as a sterilant, it may also cause a depression in the vegetative growth of the plants thus treated. For instance, a marked reduction in the elongation of the stems of wheat plants was observed after treating the wheat plants with a compound according to formula I. This effect has also been observed in other cereal plants as well as in leguminous plants, such as linseed, mustard, sugar beet and soybean. It will be clear that a depression in vegetative growth of crops — in the right stage of their development — can be very advantageous. For instance, the crops, when exposed to severe climate conditions and changes, will become less sensitive thereto.

The present invention therefore also relates to a method of depressing the vegetative growth of plants which comprises treating plants with a heterocyclic compound of the general formula I, as well as to compositions therefor. It may be very useful to achieve sterilization of the male anthers as well as depression of vegetative growth by applying only one chemical.

The dosage of heterocyclic compound applied to the plants to cause male sterility may vary over a wide range but effective results have been obtained for cereal plants by using dosages in the range of from 0.05 kg/ha to 2.00 kg/ha. Compositions containing 50 to 1,500 ppm of heterocyclic compound are very suitable for this purpose. Depressing of the growth can be suitably obtained when applying dosages in the range of from 0.05 kg/ha to 8.00 kg/ha; effective results have been obtained by using dosages in the range of from 0.1 kg/ha to 2 kg/ha.

The term "carrier" as used herein means a material, which may be inorganic or organic and of synthetic or natural origin, with which the active compound is mixed or formulated to facilitate its application to the plant, seed, soil or other object to be treated, or its storge, transport or handling. The carrier may be a solid or a fluid. Any of the materials usually employed in formulating herbicides may be used as the carrier.

Suitable solid carriers are natural and synthetic clays and silicates, for example natural silicas, such as diatomaceous earths; magnesium silicates, for example, talcs; magnesium aluminium silicates, for example, attapulgites and vermiculites; aluminium silicates, for example, kaolinites, montmorillinites and micas; calcium carbonates; calcium sulphate; synthetic hydrated silicon oxides and synthetic calcium or aluminium silicates; elements, such as for example, carbon and sulphur; natural and synthetic resins, such as for example, coumarone resins, polyvinyl chloride and styrene polymers and copolymers; solid polychlorophenols; bitumen; waxes, such as for example, beeswax, paraffin wax, and chlorinated mineral waxes; and solid fertilizers, for example superphosphates.

Examples of suitable fluid carriers are water, alcohols, such as for example, isopropanol, glycols; ketones, such as for example, acetone, methyl ethyl ketone, methyl isobutyl ketone and cyclohexanone; ethers; aromatic hydrocarbons, such as for example, benzene toluene and xylene; petroleum fractions, such as for example, kerosine, light mineral oils; chlorinated hydrocarbons, such as for example, carbon tetrachloride, perchloroethylene, trichloroethane, including liquefied normally vaporous gaseous compounds. Mixtures of differnt liquids are often suitable.

The surface-active agent may be an emulsifying agent or a dispersing agent or a wetting agent; it may be non-ionic or ionic. Any of the surface-active agents usually applied in formulating herbicides or insecticides may be used. Examples of suitable surface-active agents are the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose of pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates, such as sodium dodecyl benzene sulphonate; and polymers of ethylene oxide and copolymers of ethylene oxide and propylene oxide.

The compositions of the invention may be formulated as wettable powders dusts, granules, solutions, emulsifiable concentrates, emulsions, suspension concentrates and aerosols. Wettable powders are usually compounded to contain 25, 50 or 75%w of toxicant and usually contain, in addition to solid carrier, 3–10%w of a dispersing agent and, where necessary, 0–10%w of stabilizer(s) and/or other additives, such as penetrants or stickers. Dusts are usually formulated as a dust concentrate having a similar composition to that of a wettable powder but without a dispersant, and are diluted in the field with further solid carrier to give a composition usually containing 0.5–10%w of toxicant. Granules are usually prepared to have a size between 10 and 100 BS mesh, and may be manufactured by agglomeration or impregnation techniques. Generally, granules will contain 0.5–25%w toxicant and 0–10%w of additives, such as stabilizers, slow-release modifiers and binding agents. Emulsifiable concentrates usually contain, in addition to the solvent and, when necessary, co-solvent, 10–50%w w/v toxicant, 2–20% w/v emulsifiers and 0–20% w/v of appropriate additives, such as stabilizers, penetrants and corrosion inhibitors. Suspension concentrates are compounded so as to obtain a stable, non-sedimenting, flowable product and usually contain 10–75%w toxicant, 0.5–15%w of dispersing agents, 0.1–10%w of suspending agents, such as protective colloids and thixotropic agents, 0–10%w of appropriate additives, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

The compositions of the invention may contain other ingredients, for example, protective colloids, such as gelatin, glue, casein, gums, cellulose ethers, and polyvinyl alcohol; thixotropic agents, e.g., bentonites, sodium polyphosphates; stabilizers, such as ethylene diamine tetraacetic acid, urea, triphenyl phosphate; other herbicides or pesticides; and stickers, for example, non-volatile oils.

Aqueous dispersion and emulsions, for example compositions obtained by diluting a wettable powder or an emulsifiable concentrate according to the invention with water, also lie within the scope of the present invention. The said emulsions may be of the water-in-oil or of the oil-in-water type, and may have a thick "mayonnaise"-like consistency.

The invention is further illustrated in the following Examples, in which the terminology used to describe the growth stages in the development of cereal plants is that given in "Plant Pathology", Volume 3, 1954.

EXAMPLE I

Tests were carried out with 2-methoxy-carbonyl-3,4-methano-pyrrolidine hereinafter referred to as the sterilant on spring wheat plants, variety "Calibri".

The sterilant was applied to the plants at 2 stages of plant development, namely:

Stage 7: 2-node stage, i.e., just before the ear has become discernible as a separate organ.

Stage 10: mid-boot stage, i.e., where the ear is formed and is visible as a swelling in the enveloping leaf sheath.

Groups of plants (20 pots, 3 plants per pot) at development Stages 7 and 10 were sprayed with the sterilant as 100 ppm or 500 ppm solutions in water with added wetter (TRITON X-155; concentration 0.1%).

Control tests with plants sprayed with water and wetter only were also carried out. At ear emergence a transparent bag was placed over the ears in order to prevent cross-pollination from untreated ears. The wheat plants were allowed to set seed and the average number of wheat grains per ear were counted, the results of these counts being shown in Table I below:

TABLE I

| Experiment number | Concentration of sterilant (ppm) | Average number of grains/ear from treatment of wheat plants at | |
|---|---|---|---|
| | | Stage 7 | Stage 10 |
| Untreated control | — | 36.3 | 36.3 |
| 1 | 0 | 34.3 | 32.8 |
| 2 | 100 | 3.4 | 0.5 |
| 3 | 500 | 0 | 0 |

From these results it will be seen that the effect of the sterilant caused almost complete male sterility at 100 ppm and complete sterility at 500 ppm. Comparable trends have been observed in open-air experiments.

In order to establish that female fertility had not been substantially impaired, male sterile plants were cross-pollinated with untreated viable pollen. The seeds produced from this cross-pollination were allowed to germinate and the germination results established that the seed was 100% viable.

EXAMPLE II

Tests were carried out with 2-carboxyl-3,4-methano-pyrrolidine on wheat plants, variety "Dove".

The compound was applied to the plants at 2 stages of plant development during the stem extension period of the plant but before ear emergence, namely:

Stage 8: when the last leaf is just visible.

Stage 9: when the ligule of the last leaf is just visible.

Groups of plants (20 pots, 3 plants per pot) at development Stages 8 and 9 were sprayed with the compound as 72 ppm or 144 ppm solutions in water with added wetter (NONIDET P-40; concentration 0.1%).

Control tests with plants sprayed with water and wetter only were also carried out. At ear emergence a transparent bag was placed over the ears in order to prevent cross-pollination from untreated ears. The wheat plants were allowed to set seed and the average number of wheat grains per ear were counted, the results of these counts being shown in Table II below:

TABLE II

| Experiment number | Concentration of sterilant (ppm) | Average number of grains/ear from treatment of wheat plants at | |
|---|---|---|---|
| | | Stage 7 | Stage 10 |
| Untreated control | — | 36.3 | 36.3 |
| 1 | 0 | 34.3 | 32.8 |
| 2 | 72 | 0 | 0 |
| 3 | 144 | 0 | 0 |

These results clearly establish the sterility of the male anthers and in subsequent cross-pollination tests, the female viability was confirmed as unaffected.

EXAMPLE III

Tests were carried out with 2-carboxy-3,4-methano pyrrolidine on spring barley, variety Imber.

The sterilant was applied to the plants at development Stages 8 and 9 in the way as described in the previous Examples, with the proviso that the sterilant was applied as a 100 and 200 ppm solution in water. The results are given in Table III below:

TABLE III

| Experiment number | Concentration of sterilant (ppm) | Average number of grains/ear from treatment of wheat plants at | |
|---|---|---|---|
| | | Stage 8 | Stage 9 |
| Untreated control | — | 21.2 | 21.2 |
| 1 | 100 | 0.25 | 16.25 |
| 2 | 200 | 0 | 7.95 |

These results clearly establish the sterilizing activity of 2-carboxy-3,4-methane pyrrolidine on barley.

EXAMPLE IV

Tests were carried out with 2-carboxy-3,4-methano pyrrolidine on spring wheat, variety Sappo.

Groups of plants (10 pots, two plants per pot) at development Stages 8 and 9/10 were sprayed with the sterilant as 50 or 100 ppm solutions in water with added wetter (NONIDET P. 40; concentration 0.1%). Control tests with plants sprayed with water and wetter only were also carried out. At ear emergence a transparent bag was placed on the ears in order to prevent cross-pollination from untreated ears. The wheat plants were allowed to set seed and the average number of wheat grains per ear were counted, the results of these counts are given in Table IV below:

TABLE IV

| Experiment number | Concentration of sterilant (ppm) | Average number of grains/ear from treatment of wheat plants at | |
|---|---|---|---|
| | | Stage 8 | Stage 9/10 |
| Untreated control | — | 41.6 | 41.6 |
| 1 | 50 | 4.1 | 0.1 |
| 2 | 100 | 38.9 | 22.1 |

EXAMPLE V

Prior to harvesting the ears of the wheat plants used in the experiment described in Example I, the main height of ten randomly chosen main stems from wheat plants treated at Stage 7 was compared with that of ten control main stems of untreated plants by measuring the distance between the ear node and the base of the ear. The results are given in Table V below:

TABLE V

| Concentration of sterilant (ppm) | Average length of stem (cm) | Reduction in length (%) |
|---|---|---|
| — (control) | 33.4 | |
| 50 | 26.0 | 22.0 |
| 100 | 25.4 | 24.0 |
| 200 | 23.8 | 28.7 |

The results clearly indicate that the stem length of the wheat plants treated with 2-methoxy-carbonyl-3,4-methano pyrrolidine are markedly reduced compared with those of untreated control plants.

EXAMPLE VI

A depression in the vegetative growth was also observed when treating a number of non-cereal plants with 2-carboxy-3,4-methano pyrrolidine at a dosage rate of 0.2 and 1 kg/ha, respectively. The depression in the vegetative growth was visually recorded on a 0–8 scale, 0 indicating no reduction of growth and 8 indicating a severe reduction of growth of the plants concerned without the plants having been killed. The results of the foliar spray applications are given in Table VI below:

TABLE VI

| Dosage rate kg/ha | Maize | Rice | Barnyard grass | Oat | Linseed | Mustard | Sugar beet | Soybean |
|---|---|---|---|---|---|---|---|---|
| 1 | 1 | 5 | 5 | 6 | 6 | 5 | 7 | 8 |
| 0.2 | 0 | 2 | 2 | 3 | 5 | 3 | 5 | 8 |

EXAMPLE VII

The effect of growth depression on perennial rye grass was determined using a foliar spray of 2-carboxy-3,4-methano pyrrolidine (10 plants per treatment) as indicated in Table VII below:

TABLE VII

| Dosage rate (kg/ha) | Increase in tillers | Height (cm) | Fresh weight (g) |
|---|---|---|---|
| 0 (control) | 18 | 31 | 14 |
| 0.5 | 15 | 30 | 15 |
| 2.0 | 20 | 23 | 12 |
| 5.0 | 17 | 19 | 10 |

The results clearly indicate a marked depression of height and virtually no adverse effect on tillering, which is useful in the control of grass growth.

EXAMPLE VIII

Similar experiments as described in Example VII were carried out using the soybean cultivar "Amsoy" prior to the appearance of any flowers. The dosage rate applied and the heights of the stems recorded are given in Table VIII below:

TABLE VIII

| Dosage rate kg/ha | Height (cm) after spraying weeks | | | Increase in height (cm) over period of test |
|---|---|---|---|---|
| | 1 | 2 | 3 | |
| 0 (control) | 51 | 67 | 90 | 54 |
| 0.5 | 39 | 39 | 39 | 2 |

TABLE VIII-continued

| Dosage rate kg/ha | Height (cm) after spraying weeks | | | Increase in height (cm) over period of test |
|---|---|---|---|---|
| | 1 | 2 | 3 | |
| 1.0 | 36 | 36 | 37 | 3 |

Again, a marked reduction of the height of the stems of the plants was observed. No flowering was observed during the test period.

What I claim is:

1. A method of sterilizing male anthers in plants which comprises treating the plants with an amount effective to sterilize said anthers of a heterocyclic compound having the following general formula:

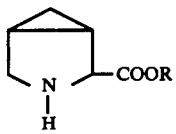

(I)

wherein R represents a hydrogen atom, an alkali metal, an alkaline earth metal, ammonium, alkylammonium the alkyl groups or groups of which preferably each contain up to 6 carbon atoms, or an alkyl group of up to 4 carbon atoms.

2. A method according to claim 1 which comprises treating cereal plants with 2-carboxy-3,4-methano-pyrrolidine or 2-methoxycarbonyl-3,4-methano-pyrrolidine.

3. A method according to claim 1 which comprises treating the plants during the period between the 2-node stage of the plant and before the emergence of the ear.

4. A method according to claim 1 which comprises treating the plants with dosages in the range of from 0.05 to 2.00 kg/ha.

* * * * *